(12) United States Patent
Horn

(10) Patent No.: US 8,999,938 B2
(45) Date of Patent: Apr. 7, 2015

(54) OPHTHALMIC LIPOPHILIC DRUG DELIVERY VEHICLE FORMULATIONS

(71) Applicant: GNT, LLC, Dana Point, CA (US)

(72) Inventor: Gerald Horn, Deerfield, IL (US)

(73) Assignee: GNT LLC, Dana Point, CA (US)

( * ) Notice: Subject to any disclaimer, the term of this patent is extended or adjusted under 35 U.S.C. 154(b) by 0 days.

(21) Appl. No.: 13/924,189

(22) Filed: Jun. 21, 2013

(65) Prior Publication Data
US 2014/0378391 A1    Dec. 25, 2014

(51) Int. Cl.
| | | |
|---|---|---|
| A61K 38/13 | (2006.01) |
| A61K 31/545 | (2006.01) |
| A01N 43/58 | (2006.01) |
| A01N 43/60 | (2006.01) |
| A61K 31/50 | (2006.01) |
| A61K 31/495 | (2006.01) |
| A01N 43/50 | (2006.01) |
| A61K 31/415 | (2006.01) |
| A61K 31/54 | (2006.01) |
| A01N 37/18 | (2006.01) |
| A61K 31/165 | (2006.01) |
| A01N 33/02 | (2006.01) |
| A01N 25/00 | (2006.01) |
| A61K 47/00 | (2006.01) |
| A61K 47/38 | (2006.01) |
| A61K 47/02 | (2006.01) |
| A61K 47/08 | (2006.01) |
| A61K 47/26 | (2006.01) |
| A61K 47/40 | (2006.01) |
| A61K 47/44 | (2006.01) |

(52) U.S. Cl.
CPC ................. *A61K 47/38* (2013.01); *A61K 47/02* (2013.01); *A61K 47/08* (2013.01); *A61K 47/26* (2013.01); *A61K 47/40* (2013.01); *A61K 47/44* (2013.01)

(58) Field of Classification Search
CPC ........ A61F 9/00; A61K 38/00; A61K 9/0048; A61K 9/08; A61K 47/38
USPC ....................................................... 514/20.5
See application file for complete search history.

(56) References Cited

U.S. PATENT DOCUMENTS

| | | |
|---|---|---|
| 5,304,569 A | 4/1994 | Lammintausta et al. |
| 5,424,078 A | 6/1995 | Dziabo et al. |
| 5,605,911 A | 2/1997 | Olney et al. |
| 5,712,301 A | 1/1998 | Heinonen et al. |
| 6,194,415 B1 | 2/2001 | Wheeler et al. |
| 6,248,741 B1 | 6/2001 | Wheeler et al. |
| 6,465,464 B2 | 10/2002 | Wheeler et al. |
| 6,562,855 B1 | 5/2003 | Franks et al. |
| 6,562,873 B2 | 5/2003 | Olejnik et al. |
| 6,627,210 B2 | 9/2003 | Olejnik et al. |
| 6,641,834 B2 | 11/2003 | Olejnik et al. |
| 6,653,354 B2 | 11/2003 | Franks et al. |
| 6,673,337 B2 | 1/2004 | Olejnik et al. |
| 6,916,811 B2 | 7/2005 | Boyle et al. |
| 7,030,149 B2 | 4/2006 | Chang et al. |
| 7,309,706 B2 | 12/2007 | Rupp et al. |
| 7,589,057 B2 | 9/2009 | Chang et al. |
| 7,678,829 B2 | 3/2010 | Matier et al. |
| 8,597,629 B1 * | 12/2013 | Horn ......................... 424/78.04 |
| 2002/0156076 A1 | 10/2002 | Chow et al. |
| 2002/0197300 A1 | 12/2002 | Schultz et al. |
| 2003/0181354 A1 | 9/2003 | Abdulrazik |
| 2003/0229088 A1 | 12/2003 | Donello et al. |
| 2004/0132824 A1 | 7/2004 | Donello et al. |
| 2004/0266776 A1 | 12/2004 | Gil et al. |
| 2005/0058696 A1 | 3/2005 | Donello et al. |
| 2005/0059664 A1 | 3/2005 | Gil et al. |
| 2005/0059744 A1 | 3/2005 | Donello et al. |
| 2005/0244468 A1 | 11/2005 | Huang et al. |
| 2005/0244474 A1 | 11/2005 | Huang et al. |
| 2006/0264442 A1 | 11/2006 | Ruiz et al. |
| 2007/0031472 A1 | 2/2007 | Huang et al. |
| 2007/0203085 A1 | 8/2007 | Lang |
| 2008/0020076 A1 | 1/2008 | Jhamandas et al. |
| 2008/0131483 A1 | 6/2008 | Abdulrazik |
| 2008/0131485 A1 | 6/2008 | Huang et al. |
| 2008/0207627 A1 | 8/2008 | Gil et al. |
| 2008/0207628 A1 | 8/2008 | Gil et al. |
| 2009/0176843 A1 | 7/2009 | Bhat et al. |
| 2009/0220611 A1 | 9/2009 | Castan et al. |
| 2010/0028266 A1 | 2/2010 | Horn |
| 2010/0029659 A1 | 2/2010 | Horn |
| 2010/0029661 A1 | 2/2010 | Horn |

(Continued)

FOREIGN PATENT DOCUMENTS

| | | |
|---|---|---|
| WO | 2010014552 | 2/2004 |
| WO | 2009022096 A1 | 2/2009 |
| WO | 2009124755 A1 | 4/2009 |

OTHER PUBLICATIONS

Olthoff, C.M.G. et al, Noncompliance with ocular hypotensive treatment in patients with glaucoma or ocular hypertension an evidence-based review, Ophthalmology. Jun. 2005;112(6):953-61.
Krupin, J.M. et al, A randomized trial of brimonidine versus timolol in preserving visual function: Results from the Low-pressure Glaucoma Treatment Study, American Journal of Ophthalmology 2011; 151: 671-681.
Gandolfi SA, et al, Effect of brimonidine on intraocular pressure in normal tension glaucoma: a short term clinical trial, Eur J Ophthalmol. Aug.-Sep. 2003;13(7):611-5.
Department of HHS FDA Center for Drug Evaluation and Research; NDA No. 21-770; Allergan Pharmaceuticals sponsor; p. 7,8.

(Continued)

*Primary Examiner* — James H Alstrum Acevedo
*Assistant Examiner* — Zachary J Miknis
(74) *Attorney, Agent, or Firm* — Wood, Phillips, Katz, Clark & Mortimer

(57) ABSTRACT

The ophthalmic drug delivery vehicles provide comfort and compliance; drug solubility, residence time and permeability; and reduce side effects. In addition, the delivery vehicle can be slightly modified to provide an artificial tear formulation.

7 Claims, No Drawings

(56) References Cited

U.S. PATENT DOCUMENTS

2010/0029662 A1 2/2010 Horn
2010/0029663 A1 2/2010 Horn

OTHER PUBLICATIONS

Toris CB et al. Arch Ophthalmol. 1995; 113(12):1514-1517. Effects of Brimonidine on Aqueous Humor Dynamics in Human Eyes.
Toris CB, Camras CB, Yablonski ME, Acute versus chronic effects of brimonidine on aqueous humor dynamics in ocular hypertensive patients, Am J Ophthalmol. 1999;128:8-14.
Berge S.M., et al., "Pharmaceutical Salts," J. Pharm. Sci., 66: 1-19 (1977).
Desai, S. and Blanchard, J. "Evaluation of Pluronic F127-based sustained-release ocular delivery systems for pilocarpine using the albino rabbit eye model," J Pharm Sci vol. 87, No. 10. Oct. 1998. p. 1190.
Mansour M, Mansour S, Mortada ND, Abd Elhady SS. Drug Dev Ind Pharm. Jul. 2008;34(7):744-52. Ocular poloxamer-based ciprofloxacin hydrochloride in situ forming gels (Abstract).
Qi H, Li L, Huang C, Li W, Wu C. Chem Pharm Bull (Tokyo). Nov. 2006;54(11):1500-7. Optimization and physicochemical characterization of thermosensitive poloxamer gel containing puerarin for ophthalmic use.
Miller S., Donovan M. International Journal of Pharmaceutics, vol. 12, Issues 2-3, Oct. 1982, pp. 147-152. Effect of poloxamer407 gel on the miotic activity of pilocarpine nitrate in rabbits.
Ricci E. J., et al.International Journal of Pharmaceutics 288 (2005) 235-244. Sustained release of lidocaine from Poloxmaer 407 gels.
Patel, JM., Formulation and Evaluation of Temperature Dependent Ophthalmic Gel Forming Solution of Brimonidine Tartrate, Intl. J. of Pharm. Chem. Sci., Oct. 2012; 1(4): 1190-1199.
Shastri DH, Praiapati ST, Patel LD. Curr Drug Deliv. Feb. 17, 2010. Studies on Poloxamer Based Mucoadhesive In situ Ophthalmic Hydrogel of Moxifloxacin HCL (Abstract).
Bhoyar BS et al. International Journal of Research in Pharmacy and Chemistry; IJRPC 2011, 1(3) p. 591-600. Design of Polyoxyethylene-Polyoxypropylene block co-polymer based in situ gelling system for localized ocular drug delivery.
Leske MC et al. "Early manifest glaucoma trial: design and baseline data," Ophthalmology, vol. 106, No. 11, pp. 2144-2153, 1999.
Schoeler M. et al. "Dexmedetomidine is neuroprotective in an in vitro model for traumatic brain injury," BMC Neurology, 12:20, 2012.
Edsman K. et al. "Rheological evaluation of poloxamer as an in situ gel for opthalmic use," European Journal of Pharmaceutical Sciences, 6(1998) 105-112.
Dumortier G. et al. "A Review of Poloxamer Pharmaceutical and Pharmacological Characteristics," Pharmaceutical Research, vol. 23, No. 12, Dec. 2006.
Feldman R. et al. "Comparison of the Ocular Hypotensive Efficacy of Adjunctive Briminodine 0.15% or Brinzolamide 1% in Combination with Travopost 0.004%," Opthamology 2007; 114:1248-1254.
Dong, C. et al. "alpha2 adrenergic receptor-mediated modulation of cytosolic Ca++ signals at the Inner Plexiform Layer of the Rat Retina," Investigative Opthamology & Visual Science, Mar. 2007, vol. 48, No. 3.
Derick RJ, Robin AL, Walters TR et al. Brimonidine tartrate. A one month dose response study. Ophthalmol 1997; 104: 131-136.
Waldock A, Snape J, Graham CM. Effects of glaucoma medications on the cardiorespiratory and intraocular pressure status of newly diagnosed glaucoma patients. Br J Ophthalmol 2000; 84(7): 710-713.
Serle J and the brimonidine study group III. A comparison of the safety and efficacy of twice daily brimonidine 0.2% versus betaxolol 0.25% in subjects with elevated intraocular pressure. Surv Ophthalmol 1996; 41 (Suppl 1): S39-S47.
Detry-Morel M, Dutrieux C. Treatment of glaucoma with brimonidine (Alphagan 0.2%). J Fr Ophtalmol 2000; 23(8): 763-768.
Cantor, LB. Brimonidine in the treatment of glaucoma and ocular hypertension, Ther Clin Risk Manag. Dec. 2006; 2 (4):337-346.

Gilsbach et al., Genetic dissection of a2-adrenoceptor functions in adrenergic versus nonadrenergic cells, Molecular Phar 2009, 75(5), p. 1160-1170.
Sato et al., In Silico Functional Profiling of Small Molecules and Its Applications, Journal of Medical Chemistry 2008, 51(24), 7705-7716 (Abstract).
Lehtimaeki et al., In vitro and in vivo profiling of fadolmidine, a novel potent a2-adrenoceptor agonist with local mode of action, European Journal of Pharmacology 2008, 599(1-3), 65-71 (Abstract).
Verbruggen et al., The effect of intravenous medetomidine on pupil size and intraocular pressure in normotensive dogs, Veterinary Quarterly 2000, 22(3), 179-180 (Abstract).
Wong et al., Design and synthesis of alpha2 adrenoceptor agonists, Book of Abstracts, 213th ACS National Meeting, San Francisco, Apr. 13-17, 1997, MEDI-023, American Chemical Society: Washington, D.C. (Abstract).
Ogidigben et al., Comparative effects of alpha-2 and DA-2 agonists on intraocular pressure in pigmented and nonpigmented rabbits, Journal of Ocular Pharmacology 1993, 9(3), 187-99 (Abstract).
MacDonald et al., Comparison of the cardiovascular effects of the a2-adrenoceptor agonist, dexmedetomidine, in rats and rabbits, Drug Development Research 1993, 28(4), 473-477 (Abstract).
Jin et al., Ocular hypotensive effects of medetomidine and its analogs, Journal of Ocular Pharmacology 1991, 7(4) 285-296 (Abstract).
Laengle et al., GLC756 decreases TNF-alpha via an alpha2 and beta2 adrenoceptor related mechanism, Experimental eye research, Nov. 2006, 83(5), 1246-1251 (Abstract).
Stamer et al., Cultured human trabecular meshwork cells express functional alpha 2A adrenergic receptors, Investigative ophthalmology & visual science Nov. 1996, 37(12), 2426-2433 (Abstract).
Pate et al., Ophthalmic arachidonylethanolamide decreases intraocular pressure in normotensive rabbits, Current eyer research Sep. 1995, 14(9), 791-797 (Abstract).
Jin et al., Ocular a2-receptor subclasses and antiglaucoma efficacy, Journal of Ocular Pharmacology, 1994, 10(1), 359-369 (Abstract).
Potter et al., Review: Alpha2 and DA2 agonists as antiglaucoma agents: Comparative pharmacology and clinical potential, Journal of Ocular Pharmacology, 1990, 6(3), 251-257 (Abstract).
Kost et al., Procedural Sedation and Analgesia in the Pediatric Emergency Department: A Review of Sedative Pharmacology, Clinical Pediatric Emergency Medicine, Dec. 2010, 11(4), 233-243 (Abstract).
Penha et al., Retinal and ocular toxicity in ocular application of drugs and chemicals—Part I: Animal models and toxicity assays, Ophthalmic Research, Jul. 2010, 44(2), 82-104 (Abstract).
Mowafi et al., Effect of dexmedetomidine premedication on the intraocular pressure changes after succinylcholine and intubation, British Journal of Anaesthesia, Apr. 2008, 100(4), 485-489.
Mowafi et al., Remifentanil obtunds intraocular pressure rises associated with suxamethonium, British Journal of Anaesthesia, Sep. 2008, 101(3), 432-433.
Bielory, Chirality in ocular agents, Current Opinion in Allergy and Clinical Immunology, Oct. 2007, 7(5), 418-423 (Abstract).
Freeman, Hypoxic-ischaemic brain injury (HIBI) after cardiopulmonary arrest, Current Anaesthesia and Critical Care, 2007, 18(5-6), 261-276 (Abstract).
Crassous et al., Interest of a2-adrenergic agonists and antagonists in clinical practice: Background, facts and perspectives, Current Topics in Medicinal Chemistry, Jan. 2007, 7(2), 187-194 (Abstract).
Gentili et al., Agonists and antagonists targeting the different a2-adrenoceptor subtypes, Current Topics in Medicinal Chemistry, Jan. 2007, 7(2), 163-186 (Abstract).
Weber et al., Neuroprotective effects of a2-adrenergic receptor agonists, Drug News and Perspectives, Apr. 2007, 20(3), 149-154 (Abstract).
Loots, Agents for sedation in ophthalmic surgery: A review of the pharmacodynamics and clinical applications, Current Anaesthesia and Critical Care, 2006, 17(3-4), 179-190 (Abstract).
Robertson, Standing sedation and pain management for ophthalmic patients, Veterinary Clinics of North America—Equine Practice, Aug. 2004, 20(2), 485-497 (Abstract).
Ruffolo et al., a-Adrenoceptors, Pharmacology and Therapeutics, 1994, 61(1-2), 1-64 (Abstract).

(56) References Cited

OTHER PUBLICATIONS

Tripathi et al., Role of receptors in the trabecular meshwork of the eye as targeted to the development of antiglacoma therapy, Drug Development Research, 1992, 27(3), 1991-228 (Abstract).

Georgiou et al., Changes in NMDA receptor contribution to synaptic transmission in the brain in a rat model of glaucoma, Neurobiology of Disease, Sep. 2010, 39(3), 344-351 (Abstract).

Schoewald et al., Relationship between Steroid Permeability across Excised Rabbit Cornea and Octanol-Water Partition Coefficients, Journal of Pharmaceutical Scienses, Jun. 1978, 67(6), 786-788.

Chang et al., Improved Corneal Penetration of Timolol by Prodrugs as a Means to Reduce Systemic Drug Load, 1987, 28(3), 487-491.

Li et al., A Study of the Relationship between Cornea Permeability and Eye Irritation Using Membrane-Interaction QSAR Analysis, Toxicological Sciences, 2005, 88(2), 434-446.

Forster, et al., Adrenergic Alpha1, and Alpha2 Binding Sites are Present in Bovine Retinal Blood Vessels, Investigative Ophthalmology & Visual Science, 1987, 28(11), 1741-1746.

Donello et al., a2-Adrenoceptor Agonists Inhibit Vitreal Glutamate and Aspartate Accumulation and Preserve Retinal Function after Transient Ischemia, Journal of Pharmacology and Experimental Therapeutics, 2011, 296(1), 216-223.

Akasu et al., Reduction of the N-Type Calcuium Current by Noradrenaline in Neurones of Rabbit Vesical Parasympathetic Ganglia, Journal of Physiology, 1990, 426, 439-452.

Trendelenburg et al., a2-Adrenoceptor-mediated inhibition of cultured sympathetic neurons: changes in a2A/D-adrenoceptor-deficient mice, Naunyn-Schmiedeberg's Arch Pharmacology, 2011, 363, 110-119.

Dong et al., a2 Adrenergic Modulation of NMDA Receptor Function as a Major Mechanism of RGC Protection in Experimental Glaucoma and Retinal Excitotoxicity, Investigative Ophthalmology & Visual Science, Oct. 2008, 49(10), 4515-4522.

Saylor et al., Experimental and Clinical Evidence for Brimonidine as an Optic Nerve and REtinal Neuroprotective Agent, Arch Ophthalmol, Apr. 2009, 127(4), 402-406.

Shirasaka et al., Activation of a G Protein-coupled Inwardly Rectifying K+ Current and Suppression of Ih Contribute to Dexmedetomidine-induced Inhibition of Rat Hypothalamic Paraventricular Nucleus Neurons, Anesthesiology, 2007, 107, 605-615.

Rosa et al., Brimonidine evokes hetrogenous vasomotor response of retinal arterioles: diminished nitric oxide-mediated vasodilation when size goes small, Am J Physiol Heart Cir Physiol 2006, 291, H231-H238.

Wirostoko et al., The Vascular Theory in Glaucoma, Glaucoma Today, Apr. 2009, 25-27.

Huang et al., The two sides of cytokine signaling and glaucomatous optic neuropathy, j ocul biol dis inform, 2009, 2, 98-103.

Hamasaki et al., Dual a2-Adrenergic Agonist and a1-Adrenergic Antagonist Actions of Dexmedetomidine on Human Isolated Endothelium-Denuded Gastroepiploic Arteries, Anesth Analg, 2002, 94, 1434-1440.

Paris et al., The Anesthetic Effects of Etomidate: Species-Specific Interaction with a2-Adrenoceptors, Anesth Analg. 2007, 105(6), 1644-1649.

Pertovaara, Antinociceptive Properties of Fadolmidine (MPV-24-26), a Novel a2-Adrenoceptor Agonist, CNS Drug Reviews, 2004, 10(2), 117-126.

Niemi et al., Synthesis, hydrolysis, and intraocular pressure lowering effects of fadolmidine prodrugs, International Journal of Pharmaceutics 2005, 29, 121-127.

Jaana Vartiainen et al, Dexmedetomidine-Induced Ocular Hypotension in Rabbits With Normal or Elevated Intraocular Pressures, Investigative Ophthalmology & Visual Science, vol. 33, No. 6, May 1992, pp. 2019-2023.

* cited by examiner

OPHTHALMIC LIPOPHILIC DRUG DELIVERY VEHICLE FORMULATIONS

BACKGROUND OF THE INVENTION

Ophthalmic drug efficacy is severely limited by non-compliance. Compliance is adversely affected by the reduced comfort, irritation, and transient quality of vision loss, which lasts minutes to tens of minutes, that is common to many drugs. In particular, these adverse effects are caused by suspensions commonly used for highly lipophilic drugs.

The fundamental challenges of ophthalmic delivery vehicles are to improve comfort; minimize visual blur on instillation; increase drug solubility; increase drug residence time and permeation through the cornea to achieve greater intraocular delivery; reduce systemic drug absorption; and cause minimal local adverse effect. Unfortunately these objectives are not met by current ophthalmic formulations.

Artificial tear vehicles may be used for drug solubilization, but do not confer increased drug residence time or offer other efficacy benefits. More viscous artificial tears use high concentrations of viscosity enhancing agents, such as Celluvisc® (Celluvisc is a registered trademark of Allergan, Inc.), high viscosity carboxymethyl cellulose (CMC) 1%—about 350 centipoise (cps) viscosity, and Refresh Liquigel® (Refresh Liquigel is a registered trademark of Allergan, Inc.), a blend of 0.35% high viscosity CMC and 0.65% low viscosity CMC—about 70 cps, but these formulations have prolonged visual blur that may last for 10 minutes or longer, greatly reducing compliance. These artificial tear vehicles also do not leach drug slowly but rather release a lot to drainage.

Gelling agents have been used with some success in increasing drug residence time and improving drug solubility. By definition such agents are instilled as liquid and then almost immediately triggered to a gel phase, where drug residence time is increased and drug release time extended. Timoptic gel (gellan gum), AzaSite® (Azasite is a registered trademark of Insite Vision, Inc.) (polycarbophil, poloxamer), and Besivance® (Besivance is a registered trademark of Bausch & Lomb, Inc.), (polycarbophil, poloxamer), 0.3% alginate Keltrol®) (Keltrol is a registered trademark of CP Kelco U.S., Inc.) are examples of such agents, where polycarbophil-poloxamer gels are commercially known as Durasite® (Durasite is a registered trademark of Insite Vision, Inc.).

However, most gelling agents: 1) increase blur on instillation; 2) cause lid and lash encrusted gel residue; 3) cause irritation/stinging on instillation; and 4) allow substantial active drug to be released systemically and may have systemic side effects. For drugs with minimal systemic side effects, or intended for only acute use of a few days, these issues are somewhat mitigated; but for drugs with higher systemic effect profiles, particularly lipophilic drugs, and more particularly as chronic use drugs, these issues can seriously affect compliance.

Gelling agents experience a phase transition to a highly viscous state, typically achieving 500-1000 cps or more after their transition. Ionic, pH, and thermal triggers are typically used. However the high shear force of each blink breaks up such phase modified films into discrete particles easily drained into the nasolacrimal duct to the nasal turbinates where residual drug may readily enter systemic circulation. Many gelling agents combine poloxamers of various molecular weights with viscosity enhancers or other gelling agents to create the desired phase transition from liquid on instillation to gel. Typically for those formulations using poloxamer without a second gelling agent, poloxamer concentrations of 15% or greater are needed to achieve gel-transition temperatures at body temperature (37° C.).

Patel (Int. J. of Pharm. Chem. Sci., Vol. 1, October-December 2012) describes the use of poloxamer and a viscosity enhancing agent—a low molecular weight, low viscosity hydroxypropylmethyl cellulose (HPMC E50LV) 1.5% with brimonidine, and demonstrates on testing concentrations of poloxamer with the HPMC from 1% to 19%, no clinically useful gelling capacity in vitro below 15%. Given the dilution of tear film, this typically requires about 21% poloxamer to achieve phase transition to gel on ophthalmic instillation. For example, Qian (Drug Dev. And Industrial Pharmacy, 2010, 36(1): 1340-1347) describes an in situ gelling system for methazolamide, a carbonic anhydrase inhibitor (glaucoma), using 21% Poloxamer 407 and 10% Poloxamer 188 to achieve a preferred phase transition to gel. High viscosity gels have been described with similar limitations to in situ gels, specifically trading off the most egregious noncompliance factors of lid and lash residue and viscous lid drag for lesser amounts of both and with less but still substantially prolonged vision blur.

Use of low viscosity agents reverses the predicament. Other compositions attempt to optimize compliance with formulations that have low viscosity agents such that comfort is good, vision is good and surface residue is absent. However, in such formulations, tear dilution is almost immediate, and drug residence time is severely limited versus in situ gels or viscous liquid gels. Therefore, formulations either improve compliance or enhance efficacy but not both. This is often seen with vehicles for dry eye. Refresh Liquigel® at 70 cps and Celluvisc® at 300 cps are such examples where vision blur is noted.

Accordingly, there remains a need for new formulations which produce greater intraocular drug permeation without compliance reducing gel crustation or blurring, and without allowing significant drug to reach systemic circulation.

BRIEF SUMMARY OF THE INVENTION

It was found that certain rheological properties of a preferred embodiment were important for the safety and efficacy of the present invention. Particularly, it was discovered that the inventive formulations create and maintain, over each blink cycle during which the drug is topically present, a very high ratio of low shear force—high viscosity and elastic modulus between blinks occurring within seconds. Yet, the inventive formulations rapidly transition to very high shear force blink phase—low viscosity and elastic modulus within a fraction of a second.

Further, between blinks, once applied, the surface thickness of the tear film/formulation is maintained at an equilibrium thin enough to prevent blurred vision.

It has been discovered that the formulations preferably have the following non-Newtonian characteristics at 37° C.:
1) creating a viscosity increase in ratio of at least about 3:1 within 1-2 seconds at the low shear force between blinks and drops within the fraction of a second to the high shear force of each blink, in a preferred embodiment, from at least 90 cps to 30 cps or less for each blink cycle;
2) on 30% dilution maintain a viscosity of about 10 cps or greater during each blink versus 1.5 cps for normal tears;
3) do not cause excessive stinging or discomfort that result in reduced compliance or unacceptable ocular surface toxicity;
4) selected excipients do not otherwise interfere with drug absorption, or otherwise reduce the activity of the active ingredient; and 5) in a preferred embodiment, a solution consisting of Poloxamer 407 5-6%, NaCl 0.25%, high blend carboxymethyl cellulose (CMC) 0.75%, but not poloxamer less than 2% or poloxamer above 12%, and not normal saline 0.9% (less effect) or 0% (stinging), and not high blend CMC of 0.5% or less or 1% or greater, and not high blend hydroxypropyl cellulose (HPC) of 1.40% or less or 1.75% or greater, created the rheological conditions necessary for both corneal retention, corneal drug release, and inhibition of systemic absorption to allow for much greater intraocular pressure (IOP) reduction at a lower concentration than any previous α-2 agonist without the local or systemic adverse events and only transient visual blur of about 90 seconds or less.

In a preferred embodiment, formulations share some or all of the following characteristics:
a) an ophthalmic lipophilic drug;
b) a high degree of intraocular lipophilicity as measured by the Log P, the equilibrated intraocular pH at 7.4, with an octanol-water partition coefficient Log P of between about 1.5 and 4.80; and more preferably between about 2.50 and 3.75 at physiologic pH; and
c) include, (i) a nonionic surfactant at a specified concentration range, and (ii) one or more specific non-Newtonian, high viscosity enhancers (also interchangeably referred to as a "gelling agents"), where typically a 1% solution is between 1,000 and 3,000 cps.

In one embodiment, the invention provides a pharmaceutical composition comprising:
i. an α-2 adrenergic receptor agonist at a concentration from between about 0.0125% to about 0.125% weight by volume, wherein said α-2 adrenergic receptor has a Log P value of 2.0 or greater and has a binding affinity of 950 fold or greater for α-2 over α-1 adrenergic receptors;
ii. a salt;
iii. a nonionic surfactant selected from a poloxamer, a polysorbate and/or cyclodextrin at a concentration of between 3% and 12% weight by volume or less; and
iv. a non-Newtonian viscosity enhancer,
wherein said pharmaceutical composition has a viscosity of between 50 and 100 cps at low shear (rotations/seconds (2/s) or less), and wherein said pharmaceutical composition is effective for the treatment of glaucoma in a patient in need thereof.

A preferred α-2 adrenergic receptor agonist is dexmedetomidine.

In one embodiment, the salt is selected from the group consisting of sodium chloride, citrate, mesylate, hydrobromide/bromide, acetate, fumarate, sulfate/bisulfate, succinate, phosphate, maleate, nitrate, tartrate, benzoate, carbonate, and pamoate.

Preferably, the salt is sodium chloride (e.g., a saline solution).

In one embodiment, the viscosity enhancer is selected from one or more of carboxymethyl cellulose, methylcellulose, hydroxymethyl cellulose, hydroxypropylmethyl cellulose, hydroxyethyl cellulose, or hydroxyethyl cellulose and hyaluronic acid; and may in addition have one or more of the polyethylene glycol (PEG), dextran, povidone, alginic acid, guar gum, acacia, Veegum® (Veegum is a registered trademark of Vanderbilt Minerals, LLC), gelatin, chitosan, Carbopol® (Carbopol is a registered trademark of Lubrizol Advanced Materials, Inc.), locust bean gum, acidic polycarbophil, dextran, pectin, glycerin, polysorbate, polyvinylpyrrolidone, and polyvinyl alcohol; such that the concentrations cumulatively do not create a phase transition to an in situ gel.

In a preferred embodiment, the viscosity enhancer is carboxymethyl cellulose.

In a preferred embodiment, the viscosity enhancer is hydroxypropyl cellulose or hydroxypropyl methyl cellulose.

Preferably, the nonionic surfactant is selected from the group consisting of Poloxamer 407, Poloxamer 188, Polysorbate 40, Polysorbate 60, Polysorbate 80 or a cyclodextrin, including but not limited to 2-hyroxypropyl-cyclodextrin (2-HP-cyclodextrin) and combinations thereof; and optionally in addition include one or more polyoxyl alkyls including but not limited to polyoxyl 40 stearate, polyoxyl 35 castor oil, and or polyoxyl dehydrogenated 40 castor oil.

Preferably, the nonionic surfactant(s) is/are present cumulatively at concentration range of 3% to 10% by weight; and more preferably, at 5% to 6% by weight.

In one embodiment, the pharmaceutical composition may further comprise a buffer which may be selected from the group consisting of citrate buffer, borate buffer, maleate buffer, succinate buffer, phosphate buffer, acetate buffer, sorbate buffer and carbonate buffer.

In one embodiment, the buffer is at a concentration between 1 mM and 100 mM.

In one embodiment the invention provides a drug delivery vehicle composition comprising:
i. sodium chloride at a concentration of 0.25% to 0.50%;
ii. a poloxamer at a concentration of between 3% and 12% weight by volume or more preferably, at 5% to 6%;
iii. carboxymethyl cellulose; and
wherein said composition has a viscosity of between 35 and 150 cps and more preferably 50 and 150 cps.

In one embodiment, the compositions of the invention may further comprise a mucoadhesive, which may be present at a concentration from between about 0.5% and about 10% weight by volume.

In one embodiment, the mucoadhesive is selected from the group consisting of carbopols, xanthan gums, and cellulose derivatives.

The most preferred vehicle composition to date (AX-100) consists of:
i) Poloxamer 407 at concentrations between 4%-7%, and more preferably from 5% to 6%;
ii) high blend HPC 1.5%;
iii) hypotonic saline 0.10%-0.80%, more preferably 0.20%-0.40%, and still more preferably 0.25%; and
iv) benzalkonium chloride (BAK) 0.02%,
wherein the pH is optionally adjusted with buffer and may be preservative free or optionally with other preservatives.

The inventive formulation may cause mild stinging with sterile water. So, adding hypotonic saline improves the comfort of the delivered formulation, eliminates stinging, and improves the ocular bioavailability.

Ophthalmic drugs for which the present invention provides a preferred vehicle include but are not limited to, any carbonic anhydrase inhibitor, particularly brinzolamide; any beta-blocker, particularly betaxolol; any α-2 agonist, particularly dexmedetomidine; or any prostaglandin, particularly bimatoprost; loteprednol; bromfenac; timolol; antibiotics; t-cell immune suppression agents like cyclosporine, lipophilic steroids, and antibiotic and steroid combinations as well as other retinal and vitreal drugs which are better administered topically such as VEGF inhibitors like tyrosine kinase inhibitors (TKI).

DETAILED DESCRIPTION OF THE INVENTION

Definitions

The term "α-2 adrenergic receptor agonists" encompasses all α-2 adrenergic receptor agonists which have a binding affinity of 1000 fold or greater for α-2 over α-1 adrenergic receptors, and more preferably 1500 fold or greater. The term also encompasses pharmaceutically acceptable salts, esters, prodrugs, and other derivatives of selective α-2 adrenergic receptor agonists.

As used herein, the term "composition" is intended to encompass a product comprising the specified ingredients in the specified amounts, as well as any product which results, directly or indirectly, from a combination of the specified ingredients in the specified amounts.

The terms "treating" and "treatment" refer to reversing, alleviating, inhibiting, or slowing the progress of the disease, disorder, or condition to which such terms apply, or one or more symptoms of such disease, disorder, or condition.

The terms "preventing" and "prevention" refer to prophylactic use to reduce the likelihood of a disease, disorder, or condition to which such term applies, or one or more symptoms of such disease, disorder, or condition. It is not necessary to achieve a 100% likelihood of prevention; it is sufficient to achieve at least a partial effect of reducing the risk of acquiring such disease, disorder, or condition.

The terms Poloxamer 407 and Pluronic® (Pluronic is a registered trademark of BASF Corporation) F127 are used interchangeably.

Unless stated otherwise, all percentages for ingredients are weight per volume (w/v).

EMBODIMENTS OF THE INVENTION

Specifically, the provided formulations comprise the following ingredients:
a) a salt (e.g., hypotonic saline, NaCl);
b) a nonionic surfactant including cyclodextrins, polysorbates, poloxamers, polyoxyl 40 stearate, polyoxyl 40 dehydrogenated castor oil, or polyoxyl 35 castor oil at a concentration at about 12% or less, and preferably between about 3% and 10%; and more preferably between about 5% and 6%; and where similarly a polysorbate up to 10% may be added or substituted to create the same cumulative concentration; polysorbates may include but are not limited to Polysorbate 40, Polysorbate 60, or Polysorbate 80 and poloxamers may include but are not limited to poloxamer 407 and 188;
c) a viscosity enhancer, preferably carboxymethyl cellulose (1%=2,500 cps) at 0.25-1.0%, and more preferably at 0.075%; or hydroxypropyl cellulose (1%=2,900 cps) 1.40% to 1.70%, more preferably 1.50% and 1.55%;
wherein the viscosity of the provided formulation is between 25 and 150 cps, and more preferably about 50 and 120 cps at 37° C.

In one embodiment, the invention provides a pharmaceutical composition comprising:
i. an ophthalmic drug at a concentration from between about 0.0125% to about 0.125% weight by volume;
ii. a salt;
iii. a nonionic surfactant at a concentration of 2-12% weight by volume; and
iv. a non-Newtonian viscosity enhancer,
wherein said pharmaceutical composition has a viscosity of between 50 and 250 cps at 20° C., and
wherein said pharmaceutical composition is effective for the treatment of glaucoma in a patient in need thereof.

Preferably, the pH of the provided compositions is within a range of 4.0 to 8.0, and more preferably from about 5.0 to about 6.0.

In one embodiment, the salt is selected from the group consisting of sodium chloride, citrate, mesylate, hydrobromide/bromide, acetate, fumarate, sulfate/bisulfate, succinate, phosphate, maleate, nitrate, tartrate, benzoate, carbonate, and pamoate.

Preferably, the salt is sodium chloride (e.g., a saline solution).

In one embodiment, the viscosity enhancer is selected from carboxymethyl cellulose, methylcellulose, hydroxymethyl cellulose, hydroxypropylmethyl cellulose, hydroxyethyl cellulose, hydroxypropyl cellulose or hyaluronate; and may have in addition one or more of polyethylene glycol, dextran, povidone, alginic acid, guar gum, acacia, Veegum®, gelatin, chitosan, Carbopol®, locust bean gum, acidic polycarbophil, dextran, pectin, povidone, polyvinylpyrrolidone, and polyvinyl alcohol.

In a preferred embodiment, the viscosity enhancer is carboxymethyl cellulose.

Preferably, the nonionic surfactant is present at concentration range of 3% to 10% by weight; and more preferably, from 5% to 6% by weight.

Preferably, the nonionic surfactant is selected from the group consisting of Poloxamer 407, Poloxamer 188. However, other poloxamers and/or combinations of various poloxamers can be used for the purposes of the present invention.

It should be understood that part of the invention and optimal formulation herein has as its goal to maximize the corneal residence time and permeability of any ophthalmic drug to achieve the greatest intraocular absorption while minimizing systemic circulation and side effects; within a narrow non-Newtonian viscosity range consistent with both these advantageous goals and excellent compliance and vision. Side effects include but are not limited to: those of the active drug, such as sedation for dexmedetomidine outside the range of the inventive formulations; decreased efficacy at concentrations below those described for the inventive compositions; greater systemic absorption; prolonged blurred vision, deposited surface lid; and/or lash viscous residue and uncomfortable viscous lid drag at concentrations above those described for inventive formulations, or when using non-inventive required excipients.

The viscosity transitions of the formulation during high and low shear force of a blink are critical to the invention because it needs to provide sufficient corneal release and retention without systemic absorption. While in situ gels provide enhanced efficacy with greater systemic side effects, liquid viscous gels and or suspensions do so similarly with considerable vision blur and viscous induced discomfort proportional to their efficacy. Mildly viscous liquids and matrix gels such as low concentration polycarbophil suspensions provide excellent vision and comfort on instillation, but at the expense of similarly enhanced efficacy. The present invention discovers a narrow range of viscosity requiring non-Newtonian viscosity excipients and nonionic surfactants where both comfort and efficacy are optimized and surprisingly systemic absorption is reduced. The ingredients and concentrations of the formulations exemplified herein are the best known examples but are not intended to be all inclusive.

It has been discovered that the inventive formulations preferably have the following non-Newtonian characteristics:
1) creating a viscosity increase in ratio of at least about 3:1 within 1-2 seconds at the low shear force between blinks and drops within the fraction of a second of each blink, in a preferred embodiment, from at least 50 cps to 20 cps or less for each blink cycle;
2) on instillation create a tear film thickness approximating normal tear film within a minute, and preferably within 30 seconds, where the between blink thickening at low shear force of each cycle is thereafter about 10μ or less, and preferably about 5μ;

3) the formulation must not cause excessive stinging or discomfort, reducing compliance or causing unacceptable ocular surface toxicity;

4) where selected incipients do not otherwise interfere with drug absorption, or otherwise reduce the activity of the active ingredient; and 5) in a preferred embodiment, a solution consisting of Poloxamer 407 between about 2% and about 12%; preferably at about 5-6%, NaCl 0.25%, high blend carboxymethyl cellulose 0.75%, created the rheological conditions necessary for both corneal retention, corneal drug release, and inhibition of systemic absorption to allow for much greater IOP reduction at a lower concentration than any previous α-2 agonist without the previously found local or systemic adverse events.

Not wishing to be held or restricted to a particular theory, it is believed that the sudden high increase in viscosity between blinks and the sudden and extremely low reduction during the fraction of a second of high shear force during a blink: 1) creates an optimal residence time on the cornea; and 2) results in a thin tear film thickness allowing excellent vision and sufficient viscous disparity between thicker low shear and thinner high shear to allow both efficacy and comfort, reduced systemic absorption and excellent vision. The low shear force rapid transition, in seconds, to very high viscosity, in addition to increasing corneal residence time, is sufficient to impede drug delivery through the nasolacrimal duct to the nasal turbinates and return to circulation without compromising vision during the blink cycle. The reduced surface tension promotes mucin penetration, and micellar formation, where induced in combination with non-Newtonian viscosity agents in a very narrow range, provide a physical and chemical shield to vascular absorption. This shield reduces the conjunctival route of systemic absorption despite prolonged residence, where a free floating surfactant monomer is more effective as a "pseudo carrier" through the amphoteric-like alternating lipophilic-hydrophilic-lipophilic layers of the cornea for permeation enhancement. These characteristics of an ophthalmic drug delivery vehicle, found in a preferred embodiment as described above, should be suitable for any soluble therapeutic or palliative ophthalmic active drug to achieve optimal vision, comfort, efficacy and safety.

In a preferred embodiment, the compositions of the invention may include the following components:

1) an ophthalmic drug at a concentration of between 0.0125% and 0.125%, most preferably 0.035% to 0.10%, weight by volume;

2) sodium chloride at a concentration of between 0 to 0.75%, more preferably 0.25% to 0.50%.

3) a nonionic surfactant, preferably, Poloxamer 407 (Pluronic® F127) or 188 or combination thereof, at a concentration of between 2% and 12%, more preferably, 5% to 6%;

4) hydroxypropyl cellulose high blend, where for 1%=2,900 cps a narrow concentration range of 1.40% to 1.70% is effective, and, for other high blend HPC, similar but slightly different narrow ranges of concentration will be found to be effective, so that the final range may slightly differ depending on molecular weight, substitutions, or use of other cellulose derivatives or other non-Newtonian viscosity excipients, and where for carboxymethyl cellulose high blend or hydroxypropyl methyl cellulose a similar narrow range is found between 0.50-0.75%; or 5) carboxymethyl cellulose high blend 0.50-0.75% and hydroxypropyl methyl cellulose 0.20%-0.50%, more preferably about 0.30% provide an initial increased blur with quicker equilibration for a preferred embodiment using dexmedetomidine as the active of about 20-30 seconds (vs. 80-90 seconds for CMC alone); and 6) optionally, benzalkonium chloride at a concentration of between 0.01% and 0.02%; preferably at 0.02%.

In one embodiment, the pharmaceutical composition may further comprise a buffer, which may be selected from the group consisting of citrate buffer, borate buffer, maleate buffer, succinate buffer, phosphate buffer, acetate buffer, sorbate buffer and carbonate buffer.

In one embodiment, the buffer is at a concentration between 1 mM and 100 mM, more preferably 4 mM to 10 mM.

In one embodiment, the pharmaceutical compositions of the invention may further comprise a mucoadhesive, which may be selected from the group consisting of carbopols, xanthan gums, and cellulose derivatives. However, other gums and/or gels, and/or viscosity enhancers can also be used for the purposes of the present invention.

In one embodiment, the mucoadhesive is at a concentration from between about 0.5% and about 1.0% weight by volume.

The inventive formulations may also optionally include other ingredients, such as corneal penetration enhancers and others.

Unexpected Results of Using the Specific Combinations of the Ingredients

The present invention combines a high degree of mucoadhesiveness, temperature sensitive alteration in rheological properties between and during blink allowing for physiologic blinking without blur, and after equilibration within about 15 to 90 seconds depending on the embodiment selected results on instillation creates a thin tear film of about 5-10 μm.

And with a variety of active lipophilic drugs, it has been surprising that the present invention:

a) creates prolonged wetting and hydration typically of about one hour or longer;

b) solubilizes lipophilic drugs;

c) enhances ocular bioavailability residence time, and absorption;

d) creates minimal blur on instillation of tens of seconds, typically 30 seconds or less;

e) produces no crusting of lids or lashes, only a prolonged wetting action felt along lid margins;

f) reduces systemic absorption; and g) allows comfortable instillations at very low (less than 4) or high (greater than 7) pH.

It has been found that deviation from the narrow range of concentrations results in either greater comfort and compliance at the expense of efficacy and greater systemic absorption where lower values are used; or poor compliance, blurred vision, viscous lid drag, surface residue but greater intraocular availability and efficacy where higher values are used. The inventive compositions discover a very narrow range using nonionic surfactant(s) and non-Newtonian viscosity excipients, where the principal benefits of an in situ gel coexist with the principal benefits of a low viscosity artificial tear for comfort and vision and where only nonionic surfactants in combination with these narrow ranges within particular ranges optimally and surprisingly reduce systemic absorption such that niosomes in a 5-100 estimated nanometer range with desired rheologic properties result and are preferred. It has also been found that a poloxamer alone, regardless of concentration, is not only ineffective for the purposes of the present invention in terms of increased efficacy, but without the ascribed combination with viscosity excipient(s) it also creates considerable stinging on topical application, whether it is buffered or non-buffered, and regardless of pH.

It would have been expected that the concentration of a poloxamer should be within the 15% to 25% range, at which gelling effect at room temperature is known to occur and/or at the physiologic range of tonicity enhancers. However, it has been discovered that a poloxamer is effective in the provided combinations when it is present at 12% or less and preferably at more than 3% but less than 10%. When a poloxamer is present at a concentration of 15% or greater or less than 2%, the compositions are surprisingly less effective or ineffective.

It was also surprising and unexpected that in tested embodiments, other gelling agents, such as Carbopol® (Carbopol is a registered trademark of Lubrizol Advanced Materials, Inc.) 954 and/or xanthan gums, could not be used instead of a poloxamer. One would have expected these agents to be interchangeable. It would have been expected that other described formulations using surfactants and viscosity excipients could be optimized for excellent vision or excellent efficacy; but the two desired advantages needed for compliant therapeutic drug delivery have previously been impossible to produce in combination despite over five decades devoted to improved ophthalmic drug delivery.

Further, the use of viscosity enhancers at too low concentrations resulted in surprisingly more side effects and reduced efficacy. It has also been found that the use of viscosity enhancers by themselves (i.e., without a poloxamer) results in much less effective formulations with more side effects.

Further, the use of viscosity enhancers at too low concentrations resulted in surprisingly more side effects and reduced efficacy, where only a few tenths of a unit of concentration could produce desired inventive formulations and only in the presence of particular viscosity excipient types and surfactant types. It has also been found that the use of viscosity enhancers by themselves (i.e., without a poloxamer) results in much less effective formulations with more side effects. Not wishing to be held to particular theory, there appears to be particular effects from the combinations of excipients and their narrow ranges that when combined allows permeation to be enhanced, systemic absorption to be decreased and lid blinks to occur without epithelial trauma. Yet, between blinks, these combinations still have sufficient improvement in viscosity over normal human tears to reduce tear dilution and optimize residence time.

Further, it has been surprisingly found that when the tonicity of the provided formulations may be greater than the usual 275 mOsm-325 mOsm and as high as 500 mOsm on instillation, the surfactant contribution may diminish within seconds presumably, not wishing to be held to particular theory, as surface tension decreases and surfactant aggregated micelles are formed. Therefore tonicity enhancement, particularly with electrolytes that alter the rheological mix, may be desired. Furthermore, the addition of such electrolyte may be critical. That is, adding surfactant to electrolyte and then with viscosity excipient appears to be different in performance than adding surfactant to viscosity excipient and then with electrolyte. For the present inventive compositions, and for purposes of consistency and reproducibility, the compositions formulated herein are added together the following order: 1) surfactant; 2) electrolyte; 3) viscosity excipient.

Lipophilicity

For any given ophthalmic drug, an optimal lipophilicity exists to maximize requisite penetration into the lipophilic cornea surface epithelium and, to a lesser extent, inner layer endothelium. If a drug is too hydrophilic, the epithelium becomes an impenetrable barrier. If a drug is too lipophilic, the drug cannot pass through the more hydrophilic stroma.

Lipophilicity may be measured, for example, using known measurements, such as Log P (log $K_{OW}$) derivation of the octanol-water partition coefficient and/or, a closely related coefficient, X Log P3-AA. see e.g., Tiejun Cheng et al, *Computation of Octanol-Water Partition Coefficients by Guiding an Additive Model with Knowledge*, J. Chem. Inf. Model., 2007, 47 (6), pp 2140-2148. These measurements represent the intraocular lipophilicity value of topical drugs for intraocular delivery (i.e., once the drug permeates into the anterior chamber and is at a pH of 7.4). A person of ordinary skill in the art is well familiar with these measurements. Thus, the Log P value is the octanol-water coefficient at pH 7.4, i.e., physiologic pH.

It was discovered in prior art that increasing the pH for certain weak base alpha 2 agonist imidazoles results in a better lipophilicity profile, making brimonidine mildly lipophilic on topical instillation and resulting in a better corneal penetration. For weak base α-2 agonists, such as brimonidine and dexmedetomidine, the more alkaline the pH, the more the equilibrium between ionized base releasing $H^+$ and non-ionized base shifts to the left (non-ionized), resulting in a more lipophilic compound. This is particularly true for α-2 agonists with pKa values of near or greater than 7.0, as is the case for brimonidine and dexmedetomidine. This is because at a more alkaline pH, more of the compound is present in a non-ionized form, and conversely, therefore, at a more acidic pH more of a drug is ionized and is less lipophilic. Usually, Log P and/or X Log P3-AA are measured when the formulation at issue is or will be at the physiologic pH of about 7.4. However where alkaline pH shifts the equilibrium favorably to non-ionic greater lipophilicity and membrane absorption for brimonidine, it has been discovered that for the much more lipophilic dexmedetomidine a similar shift at alkaline pH creates excessive lipophilicity beyond that optimal for dexmedetomidine intraocular corneal penetration, and a pH range of 4.5 to 6.5 is preferred.

For a majority of drugs, a general trend of Log P values from 2.0 to 3.0 is thought to be the best range of lipophilicity, though some of the best absorbing drugs range from 1.00 to about 2.50. Because each drug has its own Log P, and is not always amenable to stable Log D/pH manipulation, little is known about how each drug might be further optimized for topical delivery. The Log P value is highly drug/drug subclass specific, and while predictive software algorithms have been developed, there is no completely accurate means for determining the ideal Log P value for a proposed drug formulation to optimize intraocular penetration.

The range between Log P 1.5 and 2.5 typically allows for the best compromise between: a) the need for a highly lipophilic drug to penetrate the lipophilic corneal epithelium, and to a lesser extent, the very thin inner corneal membrane called Descemet's membrane, and b) a highly hydrophilic drug to penetrate the stroma, which is the middle layer of the corneal "sandwich" that must be penetrated for effective ophthalmic absorption.

The disclosed combination of a nonionic surfactant, a viscosity enhancer or combination thereof, and a hypotonic solution at the disclosed concentration ranges provides a delivery vehicle for mild to highly lipophilic drugs that is independent of pH and largely independent of the individual drug's lipophilicity.

The optimal pH of the provided formulations (i.e., the topically delivered pH of the formulation before physiologic equilibration to pH 7.4) is such pH that results in a Log "D" value for the drug (the initial topical lipophilicity) of between 0.75 and 3.08, and more preferably between 0.92 and 2.98, representing the maximum pH range of 4.0 to 8.0, and the preferred pH range of 4.5 to 7.0 for optimal comfort and stability.

Further, it has been discovered that certain buffers like highly hydrophilic phosphate buffers may render the drug less effective depending on concentration: particularly, phosphate buffer in its pH range of 6.0 to about 6.4.

However, it has been discovered that the topical application of the inventive formulations (i.e., those formulations including all of the required ingredients at the required concentrations), is not acutely pH sensitive. Further, the efficacy of the inventive formulations no longer appears to be substantially reduced by any particular buffers, including phosphate buffer. It is believed that the specific combination of the ingredients in the inventive formulations confers relative pH independence and increased solubility range on a variety of active drugs, both for glaucoma and other purposes, as well as provides increased absorption and reduced systemic side effects including but not limited to; steroidals, nonsteroidals, anti-infectives (antivirals and antimicrobials), and macular degeneration drug treatments such as anti-VEGF and more preferably tyrosine kinase inhibitors (TKI) like Cediranib, Leflunomide, Sorafenib, Pazopanib, Sunitinib, Vatalanib and Tivozanib.

Tonicity

For purposes of comfort, topical ophthalmic drugs typically require about 275 to 320 mOsm/kg tonicity. A variety of tonicity enhancers, including but not limited to electrolytes, particularly hypotonic NaCl, and less preferably polyols, such as mannitol, may be used to achieve this desired range.

It is a surprising discovery of the present invention that such comfort is enhanced when a poloxamer or other nonionic surfactant or combination of surfactants at a cumulative concentration of about 3% or above is combined with a viscosity enhancer with hypotonic electrolyte tonicity enhancement, and that poloxamer at a 3% or greater concentration is uncomfortable without additional tonicity enhancement.

Solubility

The solubility of α-2 agonists, in particular, decreases exponentially at an increased pH. Table 1 illustrates the relationship between pH and solubility in water for dexmedetomidine. It shows that the soluble concentration of dexmedetomidine falls exponentially with higher pH. For pH of 4.0 to 6.0 a very high degree of solubility exists.

TABLE 1

| pH solution | solubility (mg/ml) | max soluble concentration |
|---|---|---|
| 6.0 | 1.953 | 0.195% |
| 6.4 | ~0.60 | 0.060% |
| 7.0 | 0.224 | 0.023% |
| 7.4 | ~0.150 | 0.015% |
| 8.0 | 0.134 | 0.013% |

Similarly, cyclosporin-A has not been solubilized in aqueous solution despite decades of attempts to do so. The commercial formulation Restasis® (Restasis is a registered trademark of Allergan, Inc.), 0.05% cyclosporin-A is a polycarbophil suspension. Oily vehicles such as castor oil solubilize, but these have poor compliance. It was discovered that a preferred embodiment not only solubilized cyclosporin-A but did so at greater concentrations than 0.05%, to at least 0.20%. This is greater than required for surface treatments such as for dry eye and blepharitis or allergic conjunctivitis, but prolonged residence time of preferred embodiments may enhance dry eye therapeutic efficacy using cyclosporine, and is also potentially highly useful as an intraocular T-cell auto-immune suppression anti-inflammatory.

To achieve the greatest solubility while retaining activity, the inventive compositions should include a salt; a nonionic surfactant at a concentration of 12% weight by volume or less but more than 1%; and a viscosity enhancer. For example, using the provided compositions, dexmedetomidine is rendered soluble up to or beyond 0.15%, and cyclosporin-A at 2.0%.

It is believed the activity of the α-2 agonists, and dexmedetomidine in particular, in physiologic saline may be negatively affected by excipients of certain hydrophilicity or polarity, including citrate, various viscosity enhancing agents such as polyvinyl alcohol, various buffers such as phosphate buffer, and various gelling agents such as xanthan gum.

Thus, it is inventive and not trivial that only a very limited number of specific combinations of the ingredients lead to a greater activity and stability, and is therefore unexpectedly superior to other similar formulations.

Other agents that improve solubility which may be used for the purposes of the present invention (as long as a salt, a nonionic surfactant and a viscosity enhancers are included in the compositions) include, but are not limited to, polyanionic (multiple negatively charged) compounds, such as methylcellulose and derivatives, particularly carboxymethyl cellulose (CMC) or other cellulose derivatives; hypotonic saline; sodium acetate, calcium salt, methanesulfonate (mesylate), hydrobromide/bromide, acetate, fumarate, sulfate/bisulfate, succinate, citrate, phosphate, maleate, nitrate, tartrate, benzoate, carbonate, pamoate, borate, glycolate, pivalate, sodium citrate monohydrate, sodium citrate trihydrate, sodium carbonate, sodium ethylenediaminetetraacetic acid (EDTA), phosphoric acid, pentasodium pentetate, tetrasodium etidronate, tetrasodium pyrophosphate, diammonium ethylenediamine triacetate, hydroxyethyl-ethylenediamine triacetic acid, diethylenetriamine pentaacetic acid, nitriloacetic acid, and various other alkaline buffering salts, certain solvents such as Tween® (Tween is a registered trademark of Uniqema Americas, LLC) 20, Tween® 80, polyvinyl alcohol, propylene glycol and analogues or derivatives thereof; certain osmotic agents, such as mannitol or sucrose, hydroxypropylmethyl cellulose (HPMC) or analogues and/or derivatives thereof, or certain chelating agents.

In some preferred embodiments, the composition includes carbonate buffers where pH of about 6.0 is preferred, sodium citrate dehydrate at about 0.17%, and/or sodium acetate at about 0.39%; and/or calcium salt at about 0.048%.

Compositions and Methods of the Present Invention

Compositions and methods of the inventions encompass all isomeric forms of the described ophthalmic drugs (and particularly α-2 adrenergic receptor agonists), their racemic mixtures, enol forms, solvated and unsolvated forms, analogs, prodrugs, derivatives, including but not limited to esters and ethers, and pharmaceutically acceptable salts, including acid addition salts. Examples of suitable acids for salt formation are hydrochloric, sulfuric, phosphoric, acetic, citric, oxalic, malonic, salicylic, malic, fumaric, succinic, ascorbic, maleic, methanesulfonic, tartaric, and other mineral carboxylic acids well known to those in the art. The salts may be prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. See, e.g., S. M. Berge, et al., "Pharmaceutical Salts," *J. Pharm. Sci.*, 66: 1-19 (1977), which is incorporated herein by reference.

The compositions of the present invention are preferably formulated for a mammal, and more preferably, for a human. In one embodiment of the invention, the compositions are delivered as ophthalmic solutions into the eyes. The invention also contemplates topical compositions which include, but are not limited to, gels and creams. They may also include additional non-therapeutic components, which include, but are not limited to, preservatives, delivery vehicles, tonicity adjustors, buffers, pH adjustors, antioxidants, tenacity adjusting agents, mucoadhesive agents, viscosity adjusting agents, and water.

To make the topical compositions of the present invention, one can simply dilute more concentrated solutions, using methods known in the art with diluent of particular gelling agents in solution, being in a preferred embodiment, Poloxamer 407, Poloxamer 188, or a combination thereof. In addition, the inventive formulations may optionally include one or more of electrolytes or tonicity enhancing agents, and preferably one or more of the weak acids and/or their salts to achieve a formulated pH of 4.0 to 8.0, and more preferably 5.5 to 6.5.

One preferred method of carrying out the dilutions involves overnight refrigeration which solubilizes both the active drug and the other excipients. This is a well known technique for solubilizing drugs for use with poloxamers. However, other methods can also be used. The compositions of the invention may include various inactive ingredients commonly used in formulating topical compositions and that may improve stability of the formulation. For example, the compositions of the invention may include alcohols and/or surface active agents, including but not limited to polyglycol ether, polyethylene glycol-nonphenol ether, polyethylene glycol sorbitan monolaurate, polyethylene glycol sorbitan monooleate, polyethylene glycol sorbitanmonooleate, polyethylene glycol stearate, polyethylene glycol polypropylene glycol ether, polyvinyl alcohol, polyvinylpyrrolidone, PEG and its derivatives, including but not limited to PEG 4000 or PEG 6000, in a total amount of 0.05% to 5% by mass of the composition.

In some embodiments, the compositions of the invention may include acids or monoglycerides of fatty acids having 8 to 12 carbon atoms, which when in 0.5 to 1.5 M, and preferably equimolar concentration to the ophthalmic drug, may improve corneal permeation via ion pair formation or antioxidants such as ion-exchange/photooxidation stabilizing agents, including but not limited to citric acid, sorbic acid, boric acid, caprylic acid, glyceryl monocaprylate, glyceryl monocaproate, glycerol monolaurate, sodium metabisulfite.

In some embodiments, the compositions and methods of the present invention may include chelating agents that further improve stability, including but not limited to ethylenediaminetetraacetic acid (EDTA) and structurally related acids and even more preferably citric acid or its salt. In some embodiments, the chelating agents are present at a concentration of between 0.005% and 0.2% weight/vol.

Preservatives include, but are not limited to, benzalkonium chloride (BAK), methylparaben, polypropylparaben, chlorobutanol, thimerosal, phenylmercuric acetate, perborate, or phenylmercuric nitrate. BAK, in particular, has been found to be effective with preferred embodiments.

Tonicity adjustors include, but are not limited to, a salt such as sodium chloride, potassium chloride, dextran, cyclodextrins, mannitol, dextrose, glycerin, or another pharmaceutically or ophthalmically acceptable tonicity adjustor. In some embodiments, the tonicity modifying agents are present at a concentration of between 0.1% and 1% weight by volume.

The compositions of the present invention may comprise corneal permeation enhancing agents which include, but are not limited to, preservatives, cyclodextrins, viscosity enhancers, and ion-channel enhancing agents. In some embodiments, corneal permeation enhancing agents include citrate, a citrate salt and/or other salts which increase solubility, chelating agents such as EDTA, preservatives, ion-channeling agents, cyclodextrin, or other additives which increase corneal permeability.

In some embodiments of the invention, a corneal permeation enhancing agent may be selected from the group consisting of BAK at 0.01% to 0.02% weight by volume, EDTA at 0.005% weight by volume, caprylic acid, citric acid, boric acid, sorbic acid and/or salts, derivatives, and analogues thereof.

Many of the listed additives (for example, BAK, EDTA, etc.) may serve more than one purpose: for example, they can serve as both preservatives and corneal permeation enhancing agents (e.g. BAK), or solubilizing, preservative, and corneal permeation enhancing agents (e.g. citrate).

Buffers and pH adjustors include, but are not limited to, acetate buffers, carbonate buffers, citrate buffers, phosphate buffers and borate buffers. It is understood that various acids or bases can be used to adjust the pH of the composition as needed. pH adjusting agents include, but are not limited to, sodium hydroxide and hydrochloric acid. Antioxidants include, but are not limited to, sodium metabisulfite, sodium thiosulfate, acetylcysteine, butylated hydroxyanisole and butylated hydroxytoluene.

The following Examples are provided solely for illustrative purposes and are not meant to limit the invention in any way.

EXAMPLE 1

Preferred Embodiments

|  | (W/V %) |
|---|---|
| Formulation A | |
| Dexmedetomidine | 0.09% |
| CMC high blend | 0.75% |
| Poloxamer 407 | 5.50% |
| NaCl | 0.25% |
| BAK | 0.02% |
| Formulation B | |
| Dexmedetomidine | 0.09% |
| HPC high blend | 1.50% |
| Poloxamer 407 | 5.50% |
| NaCl | 0.25% |
| BAK | 0.02% |
| Formulation C | |
| Dexmedetomidine | 0.09% |
| CMC high blend | 0.75% |
| Polysorbate 80 | 5.50% |
| NaCl | 0.25% |
| BAK | 0.02% |

Formulation Control 1:
   Dexmedetomidine 0.01%, 0.90% NaCl, BAK 0.02%
Formulation Control 2:
   Dexmedetomidine 0.09%, HPC 1.50% high blend, 0.90% NaCl, BAK 0.02%
Protocol:
   Two drops were instilled into subject's right eye, left serving as a non-treatment eye control. Fluorescein instilled, and three applanation contacts in succession were applied prior to taking pressure readings. Successive readings were taken until three readings were all within 1 mm from maximum to minimum. Last three readings were averaged.

Results:

|  | A | B | C | D | E | Control 1 | Control 2 |
|---|---|---|---|---|---|---|---|
| Ingredients |  |  |  |  |  |  |  |
| Dexmedetomidine 0.09% | ✓ | ✓ | ✓ | ✓ | ✓ |  | ✓ |
| Dexmedetomidine 0.01% |  |  |  |  |  | ✓ |  |
| CMC high blend 0.75% | ✓ |  | ✓ | ✓ | ✓ |  |  |
| HPC high blend 1.50% |  | ✓ |  |  |  |  | ✓ |
| HPMC high blend 0.30% |  |  |  | ✓ |  |  |  |
| Poloxamer 407 | ✓ | ✓ |  | ✓ |  |  |  |
| Polysorbate 80 |  |  | ✓ |  |  |  |  |
| 2-HP-Cyclodextrin |  |  |  |  | ✓ |  |  |
| NaCl 0.25% | ✓ | ✓ | ✓ | ✓ | ✓ |  |  |
| BAK 0.02% | ✓ | ✓ | ✓ | ✓ | ✓ | ✓ | ✓ |
| NaCl 0.90% |  |  |  |  |  | ✓ | ✓ |
| Visual blur (sec) * | 80, 90 | 20, 20 | 40, 40 | 25, 25 | 20, 20 | 5, 5 | 5, 5 |
| Side effects: |  |  |  |  |  |  |  |
| Bradycardia (0-4) most | 0.0 | 0.0 | 0.0 | 0.0 | 0.0 | 0.0 | 1.5 |
| Sedation (0-4) most | 0.0 | 0.0 | 0.0 | 0.0 | 0.0 | 0.0 | 2 |
| Fatigue 0-4 (most) | 0.0 | 0.0 | 0.0 | 0.0 | 0.0 | 0.0 | 3 |
| Redness 0-4 (most) | 0.0 | 0.0 | 0.0 | 0.0 | 0.0 | 0.0 | 0.0 |
| Whitening 0-4 (most) | 1.5 | 1.5 | 1.5 | 1.5 | 2.75 | 0.5 | 1.5 |
| Comfort 0-4 (most) | 3.7 | 3.9 | 3.8 | 3.8 | 3.8 | 3.5 | 3.5 |
| Efficacy High | ✓ | ✓ | ✓ | ✓ | ✓ |  | ✓ |
| Treated Eye IOP % ↓ vs baseline, diurnal control | −38% | −31% | −29% | −38% | −40% | −20% | −40% |
| Systemic Absorption Low | ✓ | ✓ | ✓ | ✓ | ✓ |  |  |
| Non-treated Eye: IOP %↓ | −17% | −13% | −11% | −15% | −10% | −100% | −95% |
| Ratio to Treated Eye (each vs. baseline, diurnal control) |  |  |  |  |  |  |  |

* high contrast Snellen acuity; low contrast Colenbrander mixed contrast near acuity (10% Michelson)

Summary

Only the preferred embodiments A, B, C, D and E resulted in both efficacy and minimal systemic absorption, with D and E most preferred.

EXAMPLE 2

Study Design

To more fully assess ophthalmic vehicle platform efficacy, a glaucoma drug from each class of carbonic anhydrase inhibitor, beta blocker, and prostaglandins was formulated using the same formulation as in Example 1 A (preferred embodiment (PE)) and compared to the available commercial formulation, which varied from carbophil suspensions to aqueous formulations. This provided an excellent objective measure of efficacy (IOP reduction) and systemic absorption (in the non treated eye IOP reduction), and compliance (visual blur and comfort).

Protocol:

Brinzolamide 1% (Azopt® (Azopt is a registered trademark of Novartis AG) 1%); Betaxolol 0.05% (Betoptic—S 0.5%), and Bimatoprost 0.093% (Lumigan® (Lumigan is a registered trademark of Allergan, Inc.) 0.03%) were formulated as in Example 1, these drugs replacing dexmedetomidine.

Results:

|  | Drug/Formulation | | | | | |
|---|---|---|---|---|---|---|
|  | Betoptic - S 0.50% | Betaxolol 0.50% + PE | Lumigan® 0.03% | Bimatoprost 0.03% + PE | Azopt® (suspension) | Brinzolamide 1% + PE (suspension) |
| % Δ IOP ↓ | — | −43.5% | — | −34.2% | — | 7.5% |
| Treated Eye | −20.0% | −28.7% | −18.4% | −24.7% | −26.7% | −24.7% |
| Non-treated Eye/Treated Eye | −73% | 0% | 100% | 0% | 0% | 0% |
| Vision blur* | 5, 5 | 80, 90 | 5, 5 | 25, 40 | 120, 120+ | 15, 30 |

*high contrast Snellen acuity; low contrast Colenbrander mixed contrast near acuity (10% Michelson)

+Full visual recovery for Azopt ® Brinzolamide 1% suspension: 390 seconds (Alcon, commercial polycarbophil suspension) required for both Snellen 20.25 or better and low contrast 20.25 or better acuity recovery.

The preferred embodiments of the present invention delivered either, the better IOP reduction and similar vision blur or similar IOP reduction and reduced time of vision blur.

EXAMPLE 3

Preferred EmboTime from instillation until vision equilibration of the preferred embodiment (preferred embodiment as in Example 1A (PE)) versus commercial formulations, high contrast near vision Snellen acuity and low contrast Colenbrander (10% Michelson) acuity (missed contrast card set) were measured. Azopt® 1%, and Besivance® 1% served as controls, Refresh Liquigel® and Refresh® (Refresh is a registered trademark of Allergan, Inc.) Celluvisc® as published artificial viscous tears for reference.
Results:

| Visual Acuity Formulation Recovery Time | | |
|---|---|---|
| | Hi Contrast (seconds) | Low Contrast (seconds) |
| Cefazolin 3.3% + PE | 10 | 10 |
| Brinzolamide 1% + PE | 15 | 30 |
| Cyclosporin-A 2% + PE | 15 | 35 |
| Bimatoprost 0.03% + PE | 25 | 40 |
| Betaxolol 0.5% + PE | 80 | 90 |
| Brimonidine 0.20% + PE | 80 | 90 |
| Dexmedetomidine of Example 1A | 80 | 90 |
| Dexmedetomidine of Example 1B | 30 | 30 |
| Azopt ® | 390 | 390 |
| Besivance ® | 300 | 300 |
| Refresh Liquigel ® | 600 | 600 |
| Celluvisc ® | 1200 | 1200 |

(Refresh Liquigel ®, Celluvisc ® taken from published data); PE is drug in delivery formulation of Example 1A.

Discussion

All compositions of the invention performed far better in eliminating blurred vision in a matter of seconds versus actual or reported minutes for commercial ophthalmic drops.

EXAMPLE 4

Polymer Solutions, Blackburg, Va. 24060 performed rheological testing of several samples including a preferred embodiment (PE). A TA Instruments AR1000-N Rheometer was fitted with a 60 mm 2° acrylic cone and Peltier plate, with the instrument set to test temperature and allowed to equilibrate. Portions of each sample to be tested were loaded onto the instrument and conditioned at the test temperature (37 C). A steady state shear sweep was conducted with the shear rate being increased from 1 to 15,000 rotations/second.
Summary of test sample data is as follows:

| Examples | Composition | 1 rotation/ second | 1000 rotations/ second | Ratio 1/s:1000/s |
|---|---|---|---|---|
| a | Poloxamer 407 21.0%, CMC hi blend 0.75%, NaCl 0.25%, BAK 0.02% | 300,000 | 50 | 6000.0 |
| b | Poloxamer 407 12.0%, CMC hi blend 0.75%, NaCl 0.25%, BAK 0.02% | 380 | 70 | 5.4 |
| c | Poloxamer 407 5.5%, CMC hi blend 0.75%, NaCl 0.25%, BAK 0.02% | 100 | 21 | 4.8 |
| d | Bimatoprost 0.03%, Poloxamer 407 5.5%, CMC hi blend 0.75%, NaCl 0.25%, BAK 0.02% | 90 | 21 | 4.3 |
| e | Dexmedetomidine 0.09%, Poloxamer 407 5.5%, CMC hi blend 0.75%, NaCl 0.25%, BAK 0.02% | 62 | 18 | 3.4 |
| f | Dexmedetomidine 0.09%, Poloxamer 407 5.5%, CMC hi blend 0.75%, NaCl 0.25%, BAK 0.02%, 30% dilution | 20 | 10 | 2.0 |

The preferred embodiments demonstrate substantial non-Newtonian thinning at 37° C., 1000/s shear rates suggesting that upon instillation drops are viscous and will cause blurring but will have increased topical application of the drug yet will quickly clear upon blinking.

Examples 4a-c represent the platform vehicle of the invention; while examples 4d-e represent the ophthalmic compositions of the invention utilizing the platform vehicle; and example 4f represents example 4e after initial tear dilution as if administered to ones eye. The results suggest that upon administration, the vehicle and ophthalmic composition viscous but quickly go through a phase transition which causes any initial blurring to dissipate within seconds allowing the formulation to offer both enhanced viscosity over normal tears and non-Newtonian behavior well within desired limits for good vision of about 20 cps or less at high shear blink rates.

EXAMPLE 5

Preferred Embodiments with Cyclodextrin

Generally, formulations may include the following:
An ophthalmic drug such as
Dexmedetomidine 0.025%-0.125%;
2-HP-cyclodextrin 2%-12% preferably 5.5%;
A viscosity agent of 100 cps or greater such as
CMC hi blend 0.50%-0.85%, OR HPC 1.40%-1.70%, OR HPMC 0.50%-0.85%, OR CMC 0.50%-0.85% AND HPMC 0.25%-0.50%;
NaCl 0.25%;
BAK 0.01-0.02% or other preservative;
pH range 4.5-7.5 preferably pH6; and
Buffer optional.
A specific example is as follows:
Dexmedetomidine 0.09%
2-HP-cyclodextrin 5%
CMC (hi viscosity blend) 0.75%
NaCl 0.25%
BAK 0.02%
pH 6

What is claimed is:
1. An ophthalmic drug delivery composition comprising:
   a. an ophthalmic drug;
   b. from 2% to 12% w/v of one or more nonionic surfactants selected from polysorbate 80, poloxamer 407, 2-hydroxypropyl cyclodextrin, polyoxyl 40 stearate, polyoxyl 40 dehydrogenated castor oil, or polyoxyl 35 castor oil;
   c. one or more non-Newtonian high blend viscosity enhancing, non-gelling agents selected from 0.5% to

0.8% w/v carboxymethyl cellulose (1%=2,500 cps at 27° C.), from 0.5% to 0.8% w/v hydroxypropyl methyl cellulose (2%=2,653-4,719 cps at 27° C. Dow Chemical Methocel F4M Premium), from 1.4% to 1.7% w/v hydroxypropyl cellulose (1%=2,900 cps) or a combination thereof; and d. from 0.10% to 0.90% w/v NaCl, such that:

i. final composition viscosity at shear rates representative of a non-blinking eye is between 50 and 100 cps;

ii. final composition viscosity at shear rates representative of a blinking eye of less than 30 cps but remaining above 5 cps, even after 30% dilution; and iii. a final composition ratio of i./ii. of 3:1 or greater, wherein w/v denotes weight by volume.

2. An ophthalmic drug delivery composition comprising cyclosporin-A, from 4% to 7% w/v poloxamer, 0.75% w/v high blend carboxymethyl cellulose and from 0.1% to 0.9% w/v sodium chloride, wherein w/v denotes weight by volume.

3. The composition of claim 1 wherein the nonioinic surfactant is from 5% to 6% w/v poloxamer 407, and wherein the one or more non-Newtonian high blend viscosity enhancing, non-gelling agents is 0.75% w/v carboxymethyl cellulose (1%=2,500 cps at 27° C.) and wherein the sodium chloride is at a concentration of 0.25% w/v.

4. A therapeutic ophthalmic composition comprising 2% w/v cyclosporin-A, from 5% to 6% w/v poloxamer, 0.75% w/v high blend carboxymethyl cellulose and from 0.1% to 0.9% w/v sodium chloride wherein w/v denotes weight by volume.

5. A method for the treatment of ocular surface disease, selected from the group consisting of blepharitis, dry eye due to reduced tear breakup, dry eye due to reduced tear volume, corneal superficial punctate keratitis, corneal epithelial defect, and epithelial basement membrane disease, the method comprising administering to a patient in need a composition of claim 1.

6. The composition of claim 4, wherein poloxamer 407 is at a concentration of 5.5% w/v and wherein sodium chloride is at a concentration of 0.25% w/v.

7. The composition of claim 6, further comprising 0.02% w/v benzalkonium chloride.

* * * * *